United States Patent [19]
Etherington

[11] 3,978,586
[45] Sept. 7, 1976

[54] DENTAL APPARATUS

[75] Inventor: Roger F. Etherington, Newport Beach, Calif.

[73] Assignee: The Denticator Company, Inc., San Francisco, Calif.

[22] Filed: Feb. 10, 1975

[21] Appl. No.: 548,478

[52] U.S. Cl. .......................................... 32/27; 32/59
[51] Int. Cl.² .......................................... A61C 3/06
[58] Field of Search ............. 32/59, 26, 27, DIG. 1, 32/DIG. 8; 308/135, 143, 174, 175, 176, 184 R, 184 A, 26; 15/167 R, 23, 24, 25

[56] References Cited
UNITED STATES PATENTS

| 1,450,542 | 4/1923 | Faust | 15/25 |
| 1,697,534 | 1/1929 | Macready et al. | 15/23 X |
| 2,701,914 | 2/1955 | Dietrich | 32/27 |
| 3,101,542 | 8/1963 | Fodor | 32/27 |

Primary Examiner—Louis G. Mancene
Assistant Examiner—Jack Q. Lever
Attorney, Agent, or Firm—Townsend and Townsend

[57] ABSTRACT

A hand held motor driven dental prophylaxis device constructed primarily of plastic or other thin walled material is disclosed. The device includes a radially adjusting bearing circumscribing and supporting its drive shaft to minimize the imposition of side loads on the electric motor. The device also includes a switch which will operate reliably even if the apparatus is flexed or distorted.

9 Claims, 12 Drawing Figures

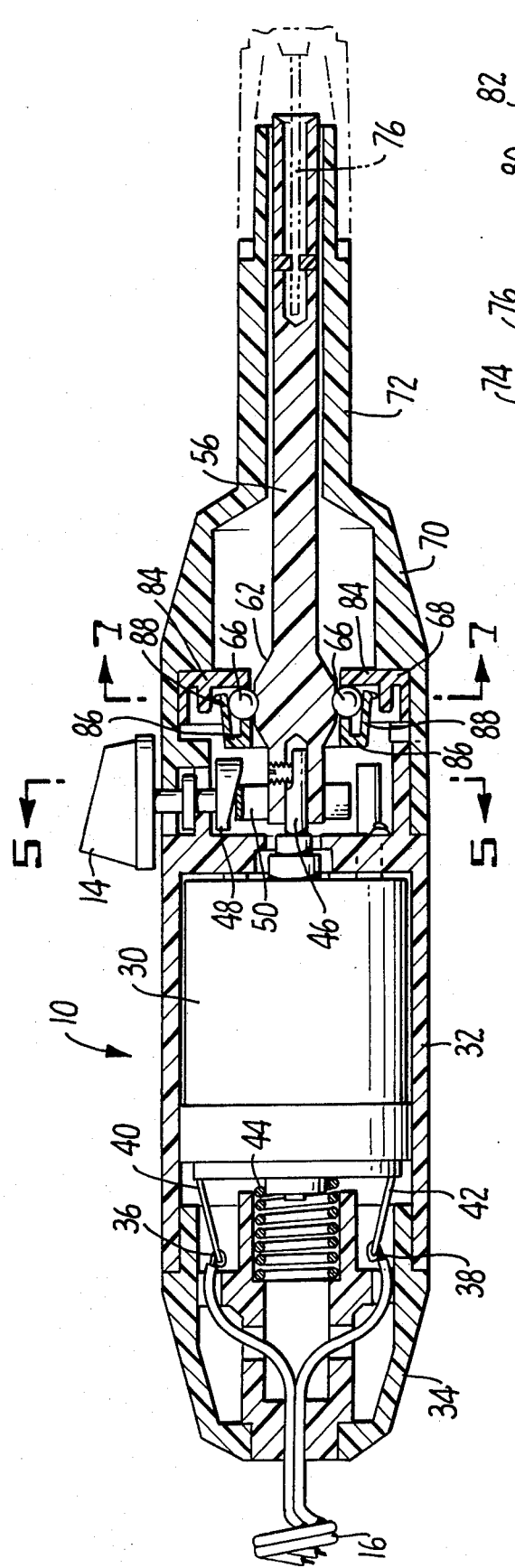
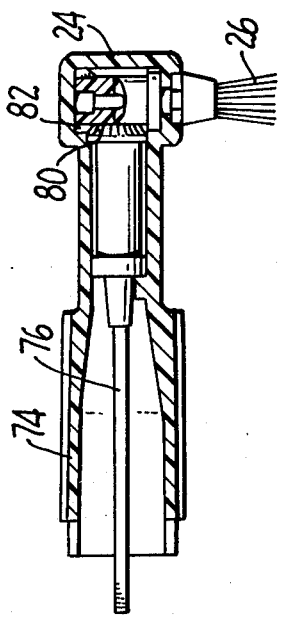
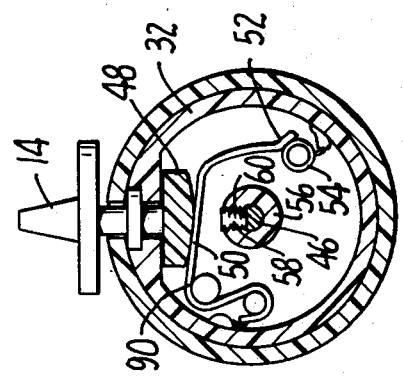
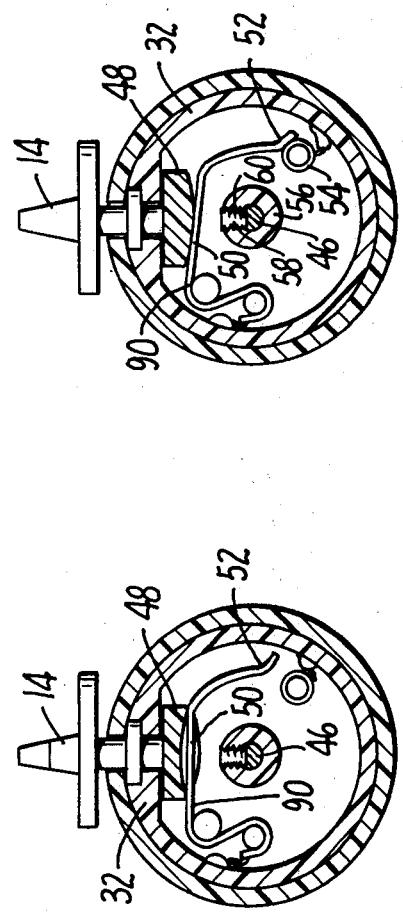

DENTAL APPARATUS

BACKGROUND OF THE INVENTION

The present invention relates to dental devices, and in particular to a hand held motor driven prophylaxis device for use in the home.

Many motorized detal instruments have been developed for home use. Such devices promote effective and efficient dental hygiene and reduce the frequency with which a dentist must be consulted. Attempts have also been made to develop a polishing instrument so that this function can be performed in the home as well. However, many difficulties have been encountered in developing such a device.

A polishing instrument for home use must be both simple and inexpensive to manufacture so that it can be produced at reasonable cost. It is thus advantageous to construct such a device from plastic material, molding the device in sections and joining the sections together. This type of structure is relatively flexible, and a bearing is required near the electric motor of the device to prevent excessive movement of the drive shaft. The drive shaft passes through a plastic shank running from the handle of the device to the polishing head, and this shank will ordinarily bend significantly when the instrument is being used because of the pressure on the polishing head.

If a ball bearing or other known type of bearing is used to fix the position of the drive shaft, the bearing will act as a fulcrum for the side loads imposed on the polishing head. The distance from the bearing to the polishing head is much greater than the distance from the bearing to the motor, and as a result, the side loads on the polishing head will be accentuated by the bearing. Relatively large side forces will thus be imposed on the electric motor, these side forces being greater than the forces imposed on the polishing head itself. Since the polishing head must be operated at relatively low speed to be effective, the electric motor has a relatively low capacity and these accentuated forces will cause the motor to bind.

SUMMARY OF THE INVENTION

The present invention provides a radially self-adjusting bearing which circumscribes the drive shaft of the prophylaxis device proximate the electric motor. The bearing includes a first outer race member which has a plurality of transverse projections spaced circumferentially about the drive shaft. A plurality of balls are located in the spaces between the respective projections in contact with the drive shaft, the projections preventing unrestricted radially inward movement of the balls. A second outer race member has a plurality of semi-rigid tabs or other bias means disposed over the balls. The tabs are normally partially flexed outwardly by the balls to bias them radially inwardly and permit limited movement of the balls radially outwardly. Transverse movement of the balls is prevented by the first and second outer race members.

When side loads are imposed on the polishing head of the device of the present invention, the bearing adjacent the electric motor will flex radially to compensate for the side loads. As a result, the bearing will not act as a pivot point for the loads and thus will not accentuate the side loads imposed on the electric motor. Excessive side loads are thus not imposed on the motor and it will not bind.

The novel features which are believed to be characteristic of the invention, both as to organization and method of operation, together with further objects and advantages thereof will be better understood from the following description considered in connection with the accompanying drawngs in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 3 is a side cross sectional view of the device of the present invention with the exception of the polishing head;

FIG. 4 is a cross sectional elevation view of the polishing head of the present invention;

FIG. 5 is a cross sectional view taken along lines 5—5 of FIG. 3;

FIG. 6 is a view similar to FIG. 5 showing the switch engaged;

DESCRIPTION OF THE PREFERRED EMBODIMENT

Figure 1:
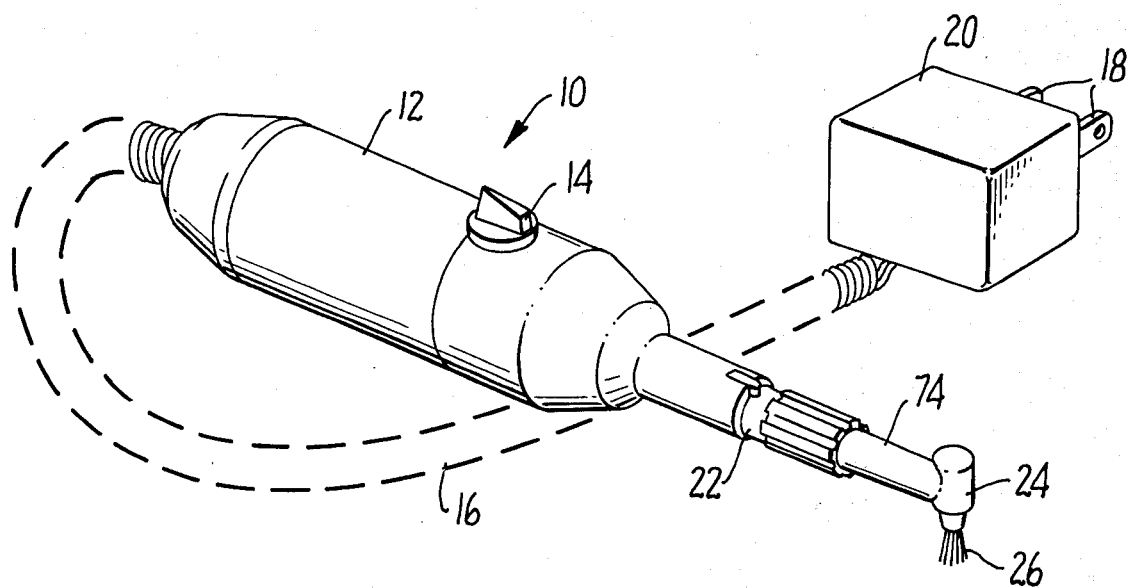
FIG. 1 is a perspective view of the apparatus of the present invention.

The prophylaxis device of the present invention is illustrated generally at 10 in FIG. 1. The device includes a handle portion 12 containing an electric motor activated by switch 14. A cord 16 couples the electric motor to a wall plug 18 which includes a transformer 20. A shank 22 extends from handle portion 12, and a polishing head 24 is located at the free end thereof. A prophylaxis tool such as a brush 26 projects from polishing head 24 in a direction transverse to shank 22.

Figure 2:
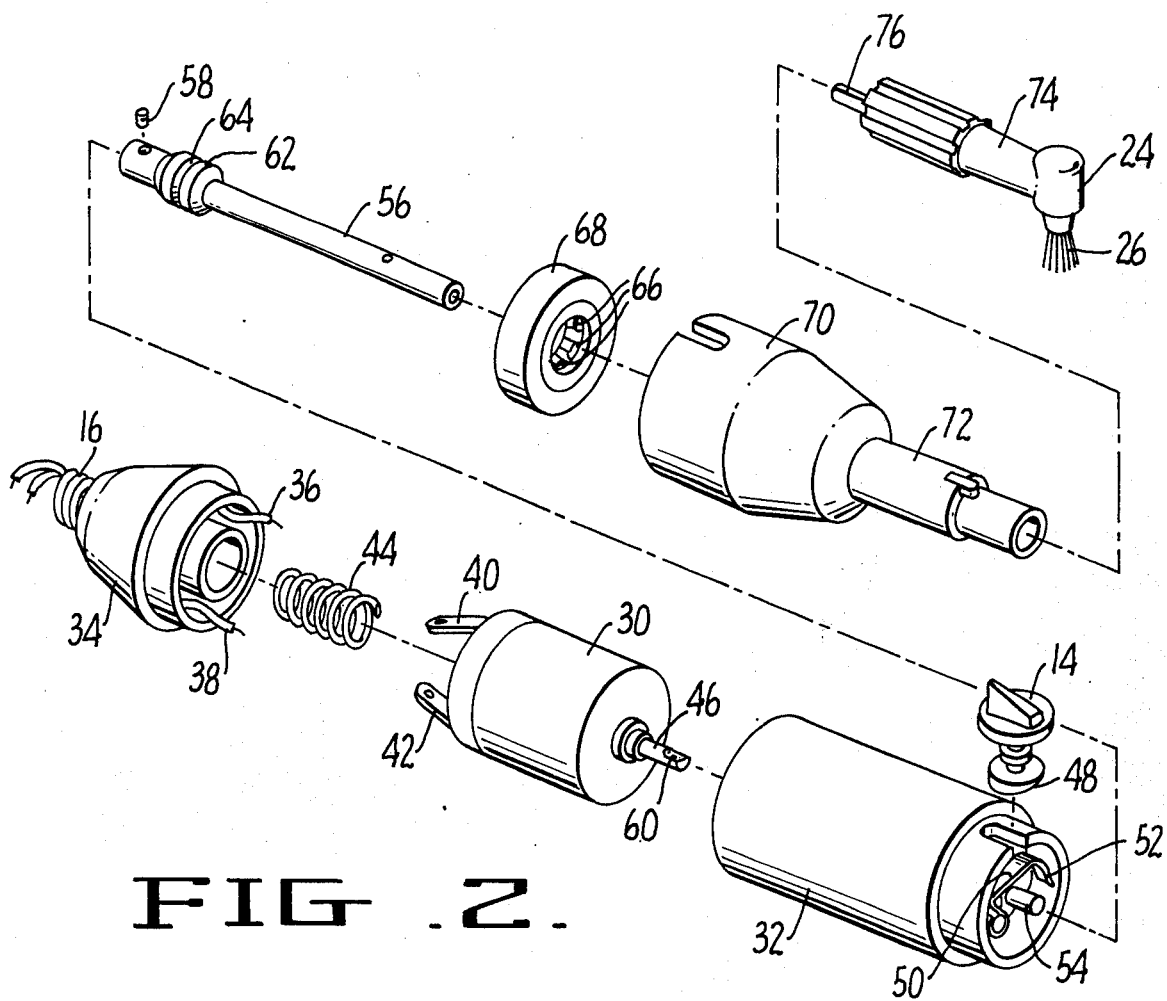
FIG. 2 is an exploded view of the dental device of the present invention.

Prophylaxis device 10 is illustrated more fully by way of reference to FIG. 2. The electric motor 30 is adapted to fit within casing 32 forming the major portion of the handle. The cord 16 enters cap 34 which is adapted to slip over the trailing end of the casing 32 and mate therewith. Cap 34, casing 32 and the remaining housing members are constructed of self-lubricating plastic to facilitate their assembly. Wire 16 is split into a pair of individual wires 36, 38 attachable to leads 40, 42 to electric motor 30. A spring 44 is provided to compensate for variations in dimensions. Electric motor 30 has a drive shaft section 46. Electric motor 30 is actuated by the depending cam portion 48 of switch 14, which depresses the cam follower portion 50 of contact 52 so that it engages pole 54, as will be illustrated further hereinafter.

A drive shaft 56 is adapted to connect to drive shaft portion 46 of motor 30. A set screw 58 is adapted to contact the flat spot 60 on drive shaft portion 46 so that they are nonrotatably interconnected. Drive shaft 56 includes an inner ball bearing race 62 having an outwardly directed circumferential groove 64. The balls 66 in outer race 68 fit in groove 64 to limit movement of drive shaft 56, as will be illustrated in more detail hereinafter. Forward cap 70 is adapted to mate with casing 32 at its leading end, and shank portion 72 projects from the forward end of forward cap 70. Polishing head 24 has a shank portion 74 adapted to mate with shank portion 72. Polishing tool 26 has a depending drive shaft portion 76 connected to drive shaft 56 to drive the polishing head with electric motor 30.

The assembled configuration of prophylaxis device 10 is illustrated in more detail by reference to FIGS. 3 and 4. Rearward cap 34 is slip-fit connected to casing 32, and wires 36, 38 are connected to leads 40, 42 which are in turn electrically coupled to motor 30. Switch 14 activates motor 30 to turn drive shaft section 46 which is in turn connected to drive shaft 56. Forward cap 70 is slip-fit over the leading end of casing 32 and circumscribes drive shaft 56. Drive shaft 56 is in turn connected to drive shaft portion 76. A plurality of gear teeth 80 at the leading end of drive shaft portion 76 engage corresponding teeth 82 and provide a right angle gear for driving polishing head 26.

Drive shaft 56 includes an inner race 62 integral to the shaft. Nonrotatable first and second outer race members 84, 86 limit the movement of balls 66 to provide a bearing generally adjacent motor 30. Due to the construction of the present invention, the shank portions 72, 74 housing drive shaft 56 are relatively flexible. Hence, side loads imposed on polishing head 26 as it is being operated must be born by drive shaft 56. If a normal bearing were used to fix the position of the drive shaft, this bearing would act as a fulcrum or pivot point, and drive shaft 56 would act as a lever. As a result, the side loads imposed on polishing head 26 would be accentuated by the bearing, and much greater side loads would be imposed on the motor. For effective polishing, polishing head 26 must be rotated at relatively low speed, and as a result motor 30 has a relatively low capacity. The accentuated side loads on the electric motor will be sufficient to bind the motor and cause it to stop. However, the bearing of the present invention includes semi-rigid tabs or other bias means 88 which allow for limited radial movement of drive shaft 56 with respect to the bearing, as will be illustrated in more detail hereinafter, so that the bearing does not act as a fulcrum and the side loads on the electric motor 30 are not accentuated. As a result, the motor will not bind and will operate efficiently even when side loads are imposed on the polishing head.

Referring next to FIG. 5, the switch 14 of the present invention has a depending cam portion 48 interior of casing 32. An electrical contact 90 is provided having a cam follower portion 50 and a contact portion 52, and the cam follower portion adapted to abut the underside of cam 48. When switch 14 is rotated as illustrated in FIG. 6, cam 48 depresses cam follower 50 downwardly so that contact portion 52 brushes against the side of pole 54. A sure contact is achieved between contact portion 52 of connector element 90 and pole 54 because of the brushing action involved, rather than the point-to-point contact usually found in such switches. Relatively loose tolerances can be accommodated by this brushing action to account for distortion of plastic casing 32, without effecting the quality of the electrical contact. In addition this brushing action will serve to maintain the contact portions clean so that they will not corrode and break the electrical connection.

Figure 7:
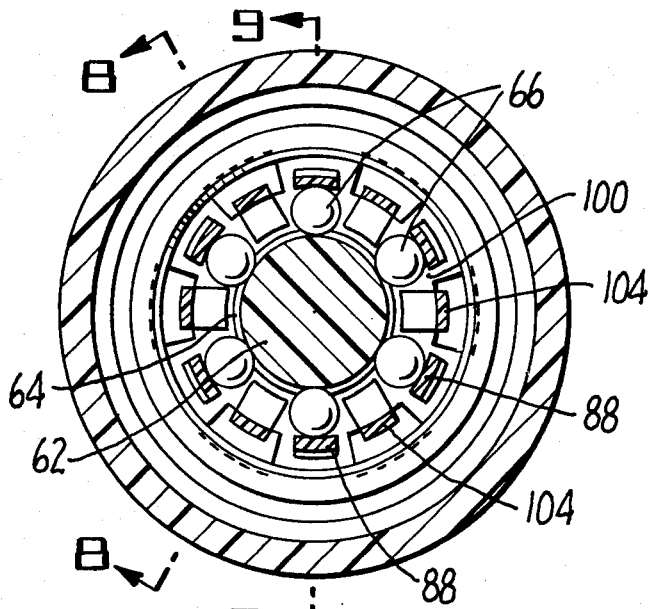
FIG. 7 is a cross sectional view taken along lines 7—7 of FIG. 3.
Figure 12:
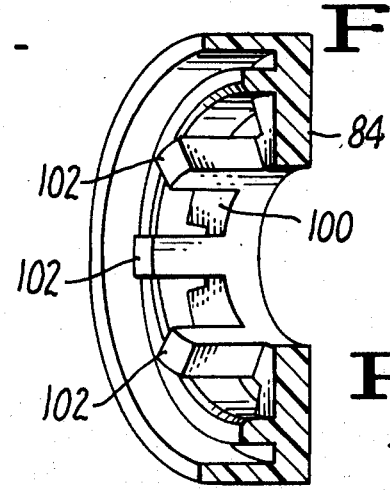
FIG. 12 is a fragmentary perspective view of the first outer race member of the present invention.

The radially adjustable bearing of the present invention is illustrated in more detail by way of reference to FIG. 7. Balls 66 fit within the groove 64 in inner race 62. The first outer race member 84 (see FIG. 12) has a radially extending wall portion 100, and a plurality of transverse projections 102 projecting from the wall portion. Transverse projections 102 allow limited inward movement of balls 66 but prevent the balls from dropping out of the outer race member when inner race 62 is not present.

Figure 8:
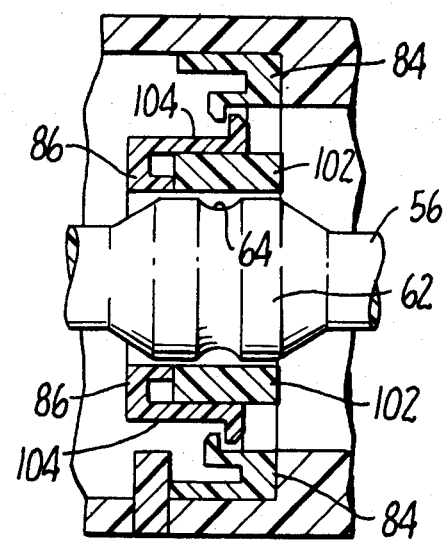
FIG. 8 is a cross sectional view taken along lines 8—8 of FIG. 7.
Figure 9:
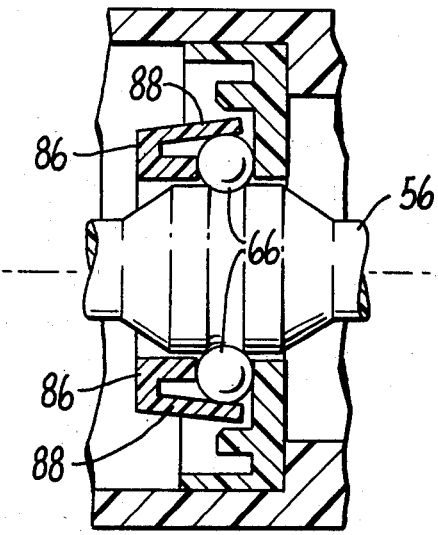
FIG. 9 is a cross sectional view taken along lines 9—9 of FIG. 7.
Figure 10:
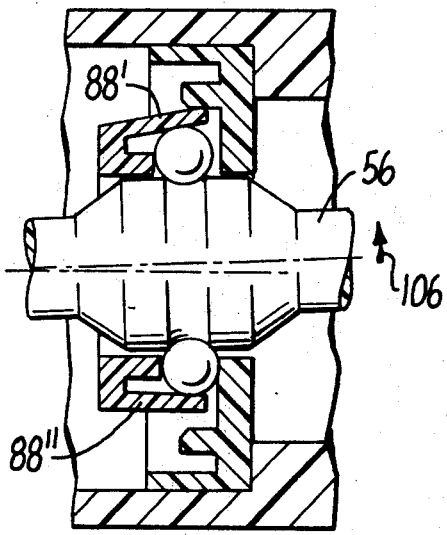
FIG. 10 is a view similar to that of FIG. 9 showing radial flexure of the bearing.
Figure 11:
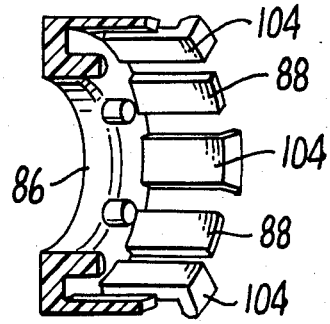
FIG. 11 is a fragmentary perspective view of the second outer race member of the present invention.

Second outer race member 86 has a plurality of flanged tabs 104 interleaved betwen semi-rigid tabs 88. Flanged tabs 104 are adapted to fit over transverse projections 102 as illustrated in FIG. 8 so that first and second outer race members 84, 86 are maintained coaxial. Semi-rigid tabs 88 in second outer race member 86 overlie the respective balls 66. When drive shaft 56 is centered in the bearing, tabs 88 are uniformly flexed outwardly to bias ball 66 inwardly. When side loads are imposed on the bearing as illustrated by arrow 106 in FIG. 10, certain of the flexible tabs such as 88' will be flexed more than other tabs such as 88'' to allow for radial adjustment of drive shaft 56 with respect to the bearing. As discussed previously, such radial adjustment will prevent the accentuation of the side loads so that the operation of the electric motor is not affected.

Although the radially adjustable bearing described above has been illustrated in the context of a prophylaxis device, it is apparent that other such uses for the radially adjustable bearing of the present invention can be made. In any situation involving a shaft supported at three or more locations, a problem is encountered in properly aligning the various bearings to avoid stress on the shaft. With the bearing of the present invention, the bearing itself will automatically align itself radially to prevent the imposition of unwanted stresses on the shaft.

While a preferred embodiment of the present invention has been illustrated in detail, it is apparent that modifications and adaptations of that embodiment will occur to those skilled in the art. For example, it may be possible to use other biasing means than the semi-rigid tabs of the present invention to inwardly bias the balls but allow for limited radially outward movement thereof. However, it is to be expressly understood that such modifications and adaptations are within the spirit and scope of the present invention, as set forth in the following claims.

What I claim as new is:

1. In a dental device comprising a casing for an electric motor, a tubular shank extending from the casing, a dental tool at the free end of the shank, and a drive shaft projecting through the shank for driving the dental tool with the electric motor, the improvement comprising a radially self-adjusting bearing circumscribing the drive shaft proximate the electric motor to minimize the imposition of side loads on the motor due to pressure exerted on the dental tool, said bearing comprising:

a first outer race member having a plurality of transverse projections spaced circumferentially about the drive shaft;

a plurality of balls located in the spaces between the respective projections in contact with the drive shaft, said projections preventing unrestricted radially inward movement of said balls; and a second outer race member having a plurality of bias means disposed over the respective balls to bias said balls radially inwardly and permit limited movement of said balls radially outwardly, said second outer race member further including means for confining the balls between the second outer race member and the first outer race member to limit transverse movement thereof.

2. A dental device as recited in claim 1 wherein the dental tool comprises a prophylaxis tool.

3. A dental device as recited in claim 1 wherein the first outer race member has a radical sidewall portion, and wherein the second outer race member has a plurality of pegs extending partially into the respective spaces between the projections opposite the sidewall portion of the first outer race member to confine the balls therebetween.

4. A dental device as recited in claim 1 wherein the bias means comprising tabs constructed of semi-rigid material.

5. A dental device as recited in claim 1 wherein the first outer race member and the second outer race member are constructed of plastic material.

6. In a dental device comprising a casing containing an electric motor and adapted to serve as a handle for manipulation of the device, a tubular shank extending from one end of the casing, a prophylaxis tool at the free end of the shank, a drive shaft extending from the motor and through the shank to drive the prophylaxis tool with the electric motor, the improvement comprising a radially self-adjusting bearing circumscribing the drive shaft proximate the electric motor to minimize the imposition of side loads on the motor due to pressure exerted on the prophylaxis tool, said bearing comprising:

an inner race circumscribing the drive shaft adjacent the electric motor and having an outwardly directed circumferential groove;

a first outer race member having a radial sidewall portion and a plurality of projections spaced circumferentially about the drive shaft and extending transversely from the sidewall portion;

a plurality of balls located in the spaces between the respective projections and projecting into the groove in the inner race, said projections preventing unrestricted radially inward movement of said balls; and a second outer race member having a plurality of semi-rigid plastic tabs disposed over the respective balls, said tabs being normally partially flexed outwardly to bias said balls radially inwardly and permit limited movement of said balls radially outwardly, said second outer race member including a plurality of pegs extending partially into the respective spaces between the projections to confine the balls between said pegs and the sidewall portion of the first outer race member.

7. A dental device comprising:

a casing adapted to serve as a handle for manipulation of the device;

an electric motor within the casing;

switch means for activating the electric motor, said switch means including a rotatable knob external of the casing, a cam internal to the casing nonrotatably connected to the knob, an electrical connector element having a cam follower portion in contact with the cam and a contact portion connector element;

a tubular shank extending from one end of the casing;

a hollow head at the free end of the shank and having an aperture disposed at a substantially right angle with respect to the shank;

a rotary prophylaxis tool extending through the aperture;

a drive shaft extending from the motor and through the shank;

right angle gear means connecting the drive shaft to the prophylaxis tool to drive the prophylaxis tool with the electric motor; and a bearing located within the casing adjacent the electric motor, said bearing comprises an inner race circumscribing the drive shaft and having an outwardly opening circumferential groove, a first outer race member having a plurality of transverse projections spaced circumferentially about the groove in the inner race member, a plurality of balls located in the spaces between the respective projections and projecting into the groove in the inner race, and a second outer race member having a plurality of semi-rigid tabs disposed over the respective balls, said tabs being normally partially flexed outwardly by the balls to bias said balls radially inwardly and permit limited movement of said balls radially outwardly, said second outer race member further including means for confining the balls between the second outer race member and the first outer race member to limit transverse movement thereof.

8. A dental device comprising an electric motor, a casing generally enclosing the electric motor, a tubular shank extending from the casing, a dental instrument at the free end of the shank, a drive shaft projecting from the motor through the shank to the dental instrument for driving the dental instrument with the electric motor, and a radially self-adjusting bearing circumscribing the drive shaft proximate the electric motor to limit movement of said drive shaft but minimize the imposition of side loads on the motor due to pressure exerted on the dental instrument.

9. A dental device as recited in claim 8 wherein the bearing comprises a first outer race member having a plurality of transverse projections spaced circumferentially about the drive shaft, a plurality of balls located in the spaces between the respective projections in contact with the drive shaft, said projections preventing unrestricted radially inward movement of said balls, and a second outer race member having a plurality of bias means disposed over the respective balls to bias said balls radially inwardly and permit limited movement of said balls radially outwardly, said second outer race member further including means for confining the balls between the second outer race member and the first outer race member to limit transverse movement thereof.

* * * * *